United States Patent [19]
Scott

[11] 3,949,764
[45] Apr. 13, 1976

[54] TREATMENT OF NATURAL AND SYNTHETIC HAIR WITH A HEAT-SETTABLE COMPOSITION
[75] Inventor: Howard L. Scott, Philadelphia, Pa.
[73] Assignees: Fabalon, Inc.; The First Foundation; Charles L. Wragg, all of Philadelphia, Pa. ; a part interest to each
[22] Filed: Nov. 3, 1970
[21] Appl. No.: 86,597

Related U.S. Application Data
[63] Continuation-in-part of Ser. No. 721,158, April 15, 1968, Pat. No. 3,568,685, which is a continuation-in-part of Ser. No. 386,730, July 31, 1964, abandoned.

[52] U.S. Cl. .................... 132/7; 8/115.6; 8/127.51; 124/DIG. 2; 424/70; 424/71; 424/78; 424/81
[51] Int. Cl.² ...................... A45D 7/06; A61K 7/09
[58] Field of Search ............ 8/127.51, 115.6; 132/7; 424/71

[56] References Cited
UNITED STATES PATENTS

| | | | |
|---|---|---|---|
| 2,570,478 | 10/1951 | Pitzl | 260/78.5 |
| 2,750,947 | 6/1956 | Gant | 424/71 X |
| 2,754,280 | 7/1956 | Brown et al. | 260/29.6 |
| 2,782,790 | 2/1957 | Hersh et al. | 424/71 X |
| 2,787,274 | 4/1957 | Gant et al. | 424/71 X |
| 3,026,250 | 3/1962 | Coyner | 424/71 X |
| 3,157,562 | 11/1964 | Kine et al. | 260/29.4 X |

*Primary Examiner*—Sam Rosen
*Assistant Examiner*—Vera C. Clarke
*Attorney, Agent, or Firm*—Arthur A. Jacobs

[57] ABSTRACT

A method of setting hair in a predetermined condition, either straightened or curled, which comprises coating the hair with a heat-settable composition containing a hardening and adhesive agent in aqueous media, either with or without the addition of separate water-proofing agents, flame-retardant agents, softening agents, and the like, and then applying heat to the coated hair to set the coated hair in the selected condition.

10 Claims, No Drawings

TREATMENT OF NATURAL AND SYNTHETIC HAIR WITH A HEAT-SETTABLE COMPOSITION

This application is a continuation-in-part of co-pending application Ser. No. 721,158, filed Apr. 15, 1968, now U.S. Pat. No. 3,568,685; the latter being a continuation-in-part of application Ser. No. 386,730, filed July 31, 1964, and now abandoned.

This invention relates to the treatment of fibers such as synthetic or natural hair, and it particularly relates to the treatment of synthetic fibers to give the appearance of human hair, as well as to the curling of straight hair or straightening of so-called "kinky" hair, either human or synthetic.

In the aforesaid parent application Ser. No. 721,158, it was indicated that the natural or synthetic hair fibers could be treated with a composition containing essentially a specific type of water-repellent agent and a specific type of substantive hardening and adhesive agent, but also preferably including a slipping agent and an emollient; and that such treatment resulted in a very satisfactory setting of the hair, either in straightened or curled form, such treated hair being resistant to the effects of moisture.

It has now been descovered that a most satisfactory treatment may be obtained by utilizing the specific type of hardening agent, by itself, as the essential treating agent, and that this will provide an effective degree of water-repellency without the use of other water-repellent agents. Preferably, however, the hardening agent is used together with certain types of softening agents which are, themselves, somewhat water-repellent. In addition, the slipping agents and emollients may also be used when desired.

Another very important consideration in treatments of both natural and synthetic hair is the elimination of fire hazards. Many prior type compositions, although otherwise satisfactory, could not be used because they were not sufficiently flame-proof. Although various types of flame-retardant agents were tried, few were satisfactory, either because they were incompatible with the hair-treating composition itself, or were dangerous to the skin or hair, or were so expensive as to be economically impractical.

In accordance with the present invention, a very satisfactory flame-retardant agent may be utilized with the hardening agent and whatever other agents of the aforementioned type are present in the composition. This flame-retardant agent is compatible with all the other agents, is free of any substantial toxicity, and is both inexpensive and in plentiful supply.

The hardening agents utilized in the present invention include those disclosed in the aforesaid parent application, namely: (1) p,p′-methylenedianiline; (2) a copolymer obtained by polymerizing a mixture of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, cyclohexyl methacrylate, p-cyclohexylphenyl methacrylate, methacrylonitrile, methyl vinyl ketone and vinyl chloride, and (c) 35–96.5% by weight of vinylidene chloride, the proportions being selected to total 100%; (3) water-insoluble copolymers obtained by the emulsion copolymerization of about 0.5–6% by weight of either N-methylolacrylamide, N-methylolmethacrylamide, or mixtures thereof with about 0.5–25% by weight of either acrylamide or methacrylamide, and having a molecular weight of 100,000 to 10,000,000; and (4) copolymers of acrylonitrile and styrene produced by Pennsylvania Industrial Chemical Corp., under the trade names "Piccoflex" and "Arolon 363" (Archer Daniels Midland Co.), a solution of a water-soluble, oxidizing resin containing about 50% by weight solids, having a viscosity of SX (Gardner Holdt at 25°C.) and a pH of between 6.9 and 7.3 at 25°C.

Another effective hardening and adhesive agent, which may also serve as a flame-retardant, is one or more of the "Geons" produced by the B. F. Goodrich Co. These include "Geon 652", a vinyl chloride-vinylidene chloride copolymer; "Geon 575 × 43" and "Geon 577", which are vinyl chloride polymers plasticized with alkyl aryl phosphate plasticizers at levels of 25 and 35 parts per hundred polymer respectively; "Geon 576", a vinyl chloride polymer plasticized with 35 parts dioctyl phthalate per 100 parts polymer; "Geon 151", "Geon 354", "Geon 352" and "Geon 351", the first of these being an unplasticized vinyl chloride homopolymer and the last three being unplasticized vinyl chloride copolymers: "Geon 450 × 167", "Geon 450 × 20", "Geon 450 × 3", "Geon 450 × 23", "Geon 460 × 1", all of which are vinyl chloride-acrylic latexes; and "Geon 552", a vinyl chloride/butadiene-acrylonitrile polyblend latex.

The hardening agent is utilized in the same proportions as in the parent application, namely, in a proportion of about 10–80% by volume of the total composition, said composition including water as at least one of the other ingredients.

A highly effective flame-retardant agent is sodium bicarbonate, and is used in a proportion of about 1–20% by volume, preferably about 1–6% by volume, of the total composition.

Other effective flame-retardant agents (which are also effective adhesive agents) are tris(2,3-dibromopropyl) phosphate, hexabromobenzene and hexabromobiphenyl. Each of these compounds is used in a 10–25% by weight concentration, preferably about 15%, in an appropriate solvent. The solvents comprise most aromatics, and some chlorinated straight chain hydrocarbons.

Among the preferable solvents are perchloroethylene, carbon tetrachloride and polyvinyl chloride. These compounds may, furthermore, be used by themselves or in admixture with either one or both of the others. In any event, they are preferably used (either as a single component or as a mixture) in a proportion of about 10–25% by volume of the total composition.

It is preferable to apply the composition, including the hardening agent and the flame-retardant agent, to the hair, as by spraying, dipping, rubbing, or the like, and then to immediately dry the treated hair at a temperature of about 120°–250°F.

As indicated above, the hardening and adhesive agent may be used by itself in aqueous media or it may be used together with the flame-retardant agent in said aqueous media (in the aforesaid range of proportions). The composition, in either case, is prepared by simple admixture, preferably under agitation, at room temperature and pressure.

Although, as stated above, the hardening and adhesive agent may be used by itself to obtain a satisfactory coating composition, it has been found that the addition of a very small amount of a softening agent materially enhances the appearance and quality of the finished product. This softening agent is generally utilized in a proportion of about 0.1–0.5% by volume of the total composition.

Among the softening agents preferably used in an aqueous dispersion of N-methylol stearamide, wherein the compound is present in the dispersion in a concentration of about 20–45% by weight, preferably about 25–30% by weight.

Another softening agent, which has a water-repellent function as well, is an aluminum complex (commercially available as DuPont's "Aluminum Complex 101"), which is a coordination of complex aluminum and myristic acid and which has the following structure:

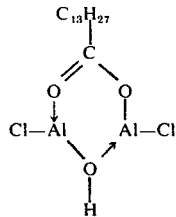

In this complex, the aluminum groups anchor to the treated surfaces while the myristic group orients outward.

Yet another softening agent is a Werner type chromium complex having the structure:

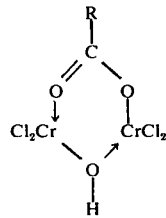

where R is either $C_{17}H_{35}$ or $C_{13}H_{27}$.

This product is commercially available as DuPont's "Quilon S" or "Quilon M", the first being the stearic acid complex and the second being the myristic acid complex.

Another commercially available chrome complex that may be used as the softening agent is that identified as DuPont's "Quilon C". This is a Werner chromium complex, usually in isopropanol solution, that differs from "Quilon S" and "Quilon M" through partial polymerization. The chromium atoms polymerize through "olation" bridges to form

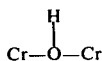

groups. On drying, hydrolysis and condensation occur to the point where the polymer is condensed through —O— bridges with the surface as follows:

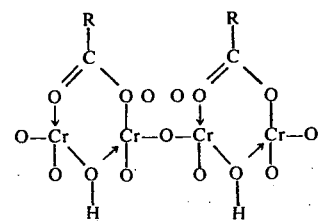

If a separate water-repellent agent is used, it is preferably one which is preferably used in a proportion of about 1–50% by volume, consists of (a) a wax-polymer emulsion wherein the ratio of wax to polymer is about 3:1, the polymer being a copolymer which consists of (1) about 15–90% by weight of an amino group containing comonomer having the structure:

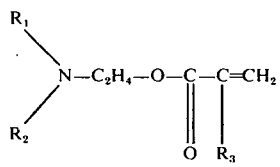

where $R_1$ and $R_2$ are selected from the group consisting of lower alkyl and cycloalkyl that include $R_1$, $R_2$, and $R_3$ is selected from the group consisting of H and $CH_3$, and (2) 10–85% by weight of a comonomer having the structure

where X is a member of the group selected from H and $CH_3$ and Y is a member selected from the polar group consisting of nitrile, aliphatic acyloxy having from 1–18 carbon atoms and alkoxycarbonyl having from 1–18 carbon atoms, said copolymer having an intrinsic viscosity in benzene at 30°C. of from 0.04–0.5.

Other products that may be used as the water-proofing or water-repellent agent are such commercially available products as "Zonyl RP" (DuPont), which is an anionic fluoro compound having a density at 77°F. of 8.85 lb/gal., a viscosity at 77°F. of 10 centipoises, a pH of 7.0 and complete solubility in water. Also "Nalan RF" and "Nalan RD" (DuPont), "Zelcon SL" (DuPont), "Zepel" (DuPont) and other similar water-dispersible products, as, for example, "Scotchgard" (Minnesota Mining & Manufacturing Co.).

The slipping agent, utilized in a proportion of about 0.1–10% by volume may be any one of a number of fluoro resins. Among these resins is a product produced by DuPont under the name of "Teflon P-TFE". This product, as used herein, is a polytetrafluoroethylene having a molecular weight of between about 1,000,000 to 10,000,000, and a viscosity greater than $10^{10}$ poises at 380°C. Also utilizable is a vinylidene fluoride resin having a molecular weight of between about 300,000 and 600,000 and having the structure:

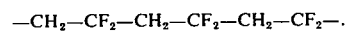

The emollient, which may be used in a proportion of from 0 to about 50.00% by volume, may be lanolin or any equivalent substance.

In the operation of the present process, the hair strands are coated with the composition, either by spraying, dipping, rubbing, etc., and the coated hair is wrapped around the device with the discs 56 and 58 acting like a comb to disentangle the hair and separate the strands into a multiplicity of hanks or groups, whereby the individual strands in each hank are more easily assessible to the heated cylindrical surface.

A sufficient amount of heat is supplied to cure the composition, effecting a crystallization thereof. This forms a relatively permanent set. The heat required for this purpose is between about 120°–250°F. depending on the type of hair or fiber being processed and on the type of composition used.

The process is repeated with each portion of the hair until the entire head of hair, wig, or the like has been treated.

The following examples illustrate the invention, without, however, limiting it except as claimed.

EXAMPLE 1

75% by volume of p,p'-methylenedianiline was mixed, at room temperature and pressure, with 3.5% by volume of sodium bicarbonate and with 21.5% water, the mixture taking place under agitation until a homogeneous cream-like substance was produced.

EXAMPLE 2

47.5 parts by weight of ethyl acrylate, 3 parts by weight of a non-ionic dispersing agent (a 70% aqueous solution of a tertoctylphenoxypolyethoxyethanol containing an average of about 35 oxyethylene units in the molecule) and 100 parts by weight of water were cooled to 15°C. and then agitated. Then 0.085 parts by weight of ammonium persulfate and 0.08 parts by weight of sodium hydrosulfite were added. As soon as the temperature began to rise, 2.5 parts by weight of itaconic acid, dissolved in 44 parts by weight of water, was added over a period of 8 minutes. As polymerization proceeded, the temperature rose in 17 minutes to a maximum of 56°C. The dispersion was stirred until it reached room temperature.

59% by volume of the above dispersion was mixed, under agitation, at room temperature and pressure, with 0.3% by volume "Aluminum Complex 101", 2% by volume sodium bicarbonate, 4% by volume of the wax-polymer emulsion described above, 1% by volume of "Teflon P-TFE", and 16.7% by volume water. Agitation was continued until a heavy grease-like cream was obtained.

EXAMPLE 3

The same ingredients, proportions and procedures were used as in Example 2, except that a 25% by weight aqueous dispersion of N-methylol stearamide was substituted for the "Aluminum Complex 101".

EXAMPLE 4

To a solution of 300 parts of 2-diethylaminoethyl methacrylate and 700 parts of octadecyl methacrylate in 1,000 parts of molten paraffin wax, maintained at 75°C., in a suitable vessel equipped with an agitator, are added 10 parts of 2,2¹-azodiisobutyronitrile in small increments over a period of 6 to 10 hours. After the last addition of the polymerization initiator, the reaction mass is held at 75°C. for two hours, and the temperature is then raised to 100°C. and held at that temperature for about one-half hour. The charge is then diluted with 2,000 parts by weight of molten paraffin wax, to give a wax:copolymer ration of 3:1. All parts herein are by weight.

Into 100 parts by weight of the above wax-copolymer composition, melted by heating to between 65° and 70°C., 4 parts by weight of glacial acetic acid are stirred. The wax - copolymer mass is then slowly added to 294 parts by weight of water kept under vigorous agitation with a high shear mixer, and maintained at 65° to 70°C. Agitation is then continued for a sufficient time to complete the emulsification. The resulting product is then cooled to room temperature. The product has a molecular weight of between about 20,000 and 80,000 and a viscosity of about 16 centipoises at 80°F. (Brookfield).

12% by volume of the above emulsion was mixed with 67.5% by volume of p,p'-methylenedianiline, 0.5% by volume "Teflon P-TFE" having a molecular weight of about 1,500,000, and 20% by volume lanolin. Three drops of perfume were then added. The mixture was thoroughly agitated at room temperature and pressure until a homogeneous, grease-like cream was produced.

In one operation, the composition of Example 1 was applied to a human head of hair by rubbing a sufficient quantity into the hair until the hair was completely coated. Thereafter, each increment of the hair was heated to 160°F. for about 5 seconds at which time crystallization of the composition occurred. After the entire head of hair had been processed, the treated hair was styled in a desirable manner.

In the same manner, the compositions of Examples 2, 3, and 4 were applied to other human heads of hair, the same procedure and time of heating being used.

In the same manner, the compositions of Examples 1, 2, 3, and 4 were applied to wigs consisting of nylon strands. After treatment, each wig was styled in the desired manner.

The invention claimed is:

1. A hair treating composition comprising a hardening and adhesive agent and a flame-retardant agent in an aqueous medium, the hardening and adhesive agent being in a concentration of about 10–80% by volume and being selected from the group consisting of (1) p,p'-methylenedianiline; (2) a copolymer of (a) about 0.5–25% by weight of itaconic acid, (b) 3–4% by weight of at least one polymerizable compound selected from the group consisting of acrylonitrile, alkyl esters of acrylic and methacrylic acids having from 1 to 18 carbon atoms in the alkyl group, phenyl methacrylate, cyclohexyl methacrylate, p-cyclohexyl-phenyl methacrylate, methacrylonitrile, methyl vinyl ketone and vinyl chloride, and (c) 35–96.5% by weight of vinylidene chloride, the proportions being selected to total 100%; (3) a copolymer of acrylonitrile and styrene wherein a 50% by weight solution has a viscosity of SX (Gardner Holdt) at 25°C; and (4) vinyl chloride polymer latex; said flame-retardant agent being present in about 1–25% by volume and being selected from the group consisting of sodium bicarbonate, tris-(2,3-dibromo-propyl) phosphate, hexabromobenzene and hexabromobiphenyl.

2. The composition of claim 1 also including a softening agent, said softening agent being present in a proportion of about 0.1–0.5% by volume and being selected from the group consisting of (a) N-methylol stearamide, (b) a compound having the formula:

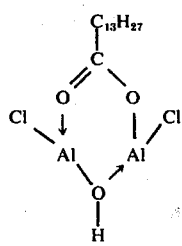

(c) a compound having the formula:

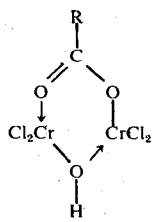

wherein R is $C_{13}H_{27}$ or $C_{17}H_{35}$, and (d) a compound having the formula:

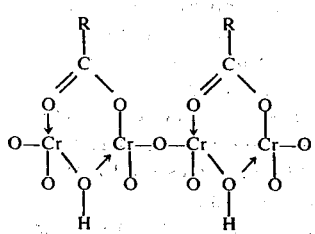

wherein R is $C_{13}H_{27}$ or $C_{17}H_{35}$.

3. The composition of claim 1 also including about 1-50% by volume of a paraffin wax-polymer emulsion wherein the ratio of wax to polymer is about 3:1, the polymer being a copolymer which consists of (1) about 15-90% by weight of an amino group containing comonomer having the structure

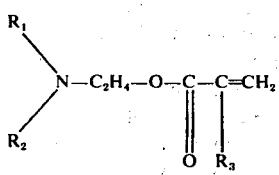

where $R_1$ and $R_2$ are selected from the group consisting of lower alkyl and cycloalkyl that include $R_1$, $R_2$, and $R_3$ is selected from the group consisting of H and $CH_3$, and (2) 10-85% by weight of a comonomer having the structure:

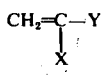

where X is a member of the group selected from H and $CH_3$ and Y is a member selected from the polar group consisting of nitrile, aliphatic acyloxy having from 1-18 carbon atoms and alkoxycarbonyl having from 1-18 carbon atoms, said copolymer having an intrinsic viscosity in benzene at 30°C. of from 0.04-0.5.

4. The composition of claim 2 also including about 1-50% by volume of a paraffin wax-polymer emulsion wherein the ratio of wax to polymer is about 3:1, the polymer being a copolymer which consists of (1) about 15-90% by weight of an amino group containing comonomer having the structure:

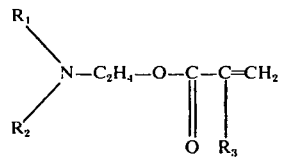

where $R_1$ and $R_2$ are selected from the group consisting of lower alkyl and cycloalkyl that include $R_1$, $R_2$, $R_3$ is selected from the group consisting of H and $CH_3$, and (2) 10-85% by weight of a comonomer having the structure:

$$CH_2=C-Y \\ \phantom{CH_2=}X$$

where X is a member of the group selected from H and $CH_3$ and Y is a member selected from the polar group consisting of nitrile, aliphatic acyloxy having from 1-18 carbon atoms and alkoxycarbonyl having from 1-18 carbon atoms, said copolymer having an intrinsic viscosity in benzene at 30°C, of from 0.04-0.5.

5. The composition of claim 1 also including about 0.1-10% by volume of a member of the group selected from (a) polytetrafluoroethylene having a molecular weight of between about 1,000,000 to 10,000,000, and a viscosity greater than $10^{10}$ poises at 380°C., and (b) vinylidene fluoride resin having a molecular weight of between about 300,000 and 600,000 and having the structure:

$$-CH_2-CF_2-CH_2-CF_2-CH_2-CF_2-.$$

6. A method of treating hair which comprises coating the hair with an effective amount sufficient to set the hair of the composition of claim 1 and then heating the coated hair to a temperature of about 120°-250°F.

7. A method of treating hair which comprises coating the hair with an effective amount sufficient to set the hair of the composition of claim 2 and then heating the coated hair to a temperature of about 120°-250°F.

8. A method of treating hair which comprises coating the hair with an effective amount sufficient to set the hair of the composition of claim 3 and then heating the coated hair to a temperature of about 120°-250°F.

9. A method of treating hair which comprises coating the hair with an effective amount sufficient to set the hair of the composition of claim 4 and then heating the coated hair to a temperature of about 120°-250°F.

10. A method of treating hair which comprises coating the hair with an effective amount sufficient to set the hair of the composition of claim 5 and then heating the coated hair to a temperature of about 120°-250°F.

* * * * *